United States Patent [19]

Meredith

[11] Patent Number: 4,577,635
[45] Date of Patent: Mar. 25, 1986

[54] MEDICAL INSTRUMENT

[75] Inventor: Hadyn G. Meredith, London, Great Britain

[73] Assignee: Rocket of London Limited, Watford, Great Britain

[21] Appl. No.: 564,164

[22] Filed: Dec. 22, 1983

[30] Foreign Application Priority Data

Dec. 30, 1982 [GB] United Kingdom ............... 8236922

[51] Int. Cl.[4] .............................................. A61B 5/04
[52] U.S. Cl. .................................................. 128/642
[58] Field of Search ....................... 128/642, 784–786, 128/419 P

[56] References Cited

U.S. PATENT DOCUMENTS

| 4,180,080 | 12/1979 | Murphy | 128/642 |
| 4,301,806 | 11/1981 | Helfer | 128/642 |
| 4,321,931 | 3/1982 | Hon | 128/642 |
| 4,437,467 | 3/1984 | Helfer et al. | 128/642 |

FOREIGN PATENT DOCUMENTS 2738479  3/1979  Fed. Rep. of Germany ...... 128/642

Primary Examiner—Lee S. Cohen
Attorney, Agent, or Firm—Mason, Fenwick & Lawrence

[57] ABSTRACT

A medical instrument for monitoring fetal heart rate and having an electrode for insertion by rotation in the fetal head, and a torque limiting device for preventing over-penetration of the electrode. The torque limiting device is preferably a helical spring rotatable with the electrode at low torque and arranged to disengage from frictional driving contact at the torque limit.

4 Claims, 5 Drawing Figures

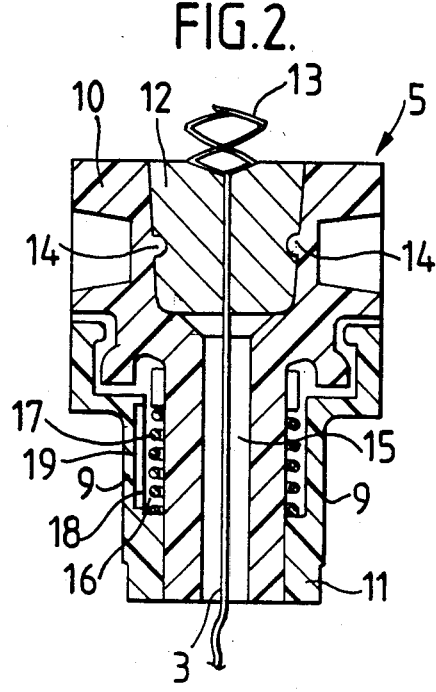
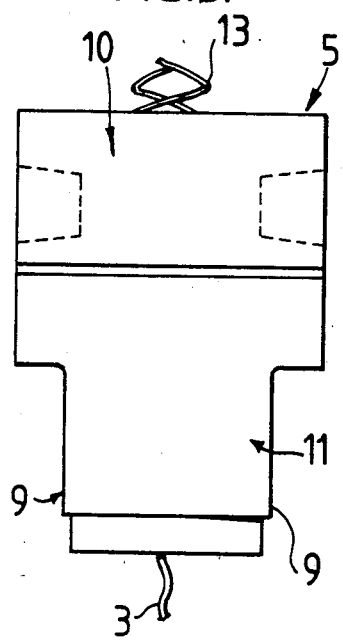
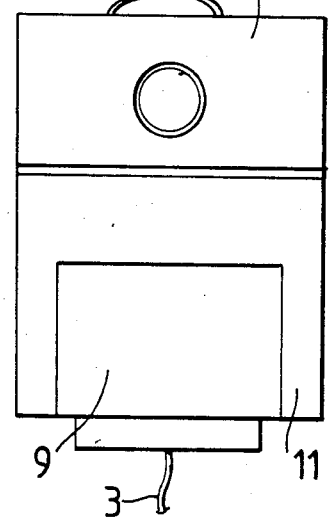
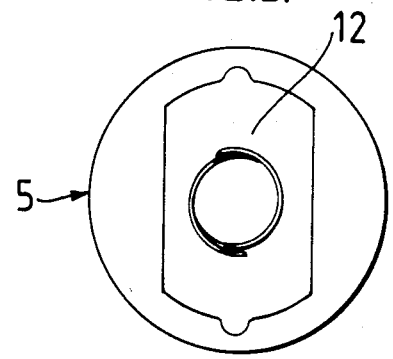

MEDICAL INSTRUMENT

BACKGROUND OF THE INVENTION

This invention relates to a medical instrument.

The usefulness of obtaining a complete record of fetal heart rate during delivery is now recognized extensively in the Western world. Sometimes it is used routinely and becomes part of the general birth record and more significantly it is used with babies at risk. By linking the heart rate with contractions and cervical dilatation etc., an obstetrician has an early warning of fetal distress and is then well placed to deal with it at the outset. The first successful device took the form of an insulated suture clip which could be attached to the fetal head and complete an electrical circuit with a second electrode in contact with the mother.

Later modifications of such a device included at the leading end a helical electrode which was attached to the foetal scalp by rotation of an applicator, this motion being transferred to the electrode causing it to advance helically. A double helix has also been used at the leading end for a uniform approach to the fetal scalp. However, a problem with such previously-proposed devices was that over-rotation of the helical electrode could traumatise the foetal scalp or bend the electrode beneath the surface, making removal difficult. Damage could thus be caused to the fetus.

SUMMARY OF THE INVENTION

According to the present invention there is provided a medical instrument for fetal monitoring comprising an electrical conductor for insertion in the fetal scalp, a handle connected to the conductor for rotation of the conductor to cause it to penetrate the scalp, and a torque limiting device which limits the amount of torque which can be applied to the conductor by the handle.

Preferably, the torque limiting device comprises a member which is resiliently deformable between a first configuration in which it provides a driving link between the handle and the conductor on application of torque to the handle below a predetermined limiting value and a second configuration in which the driving link is broken on application of torque to the handle above the predetermined limiting value.

Such an arrangement may be provided by a helical spring which is in frictional driving connection with the conductor or with the handle so as to rotate therewith at low levels of applied torque, the spring being held against rotation relative to the handle or to the conductor respectively, in a manner whereby application of torque to the handle above the predetermined limiting value causes the frictional driving connection to be released.

The helical spring preferably extends between inner and outer walls of an annular passageway, one of the walls being rotatable with the handle and the other being rotatable with the conductor, whereby the spring is held positively against rotation relative to one of the walls and frictionally against rotation relative to the other. Application of torque to the handle causes the spring to deform by increasing or decreasing its diameter, due to the "coiling" or "uncoiling" effect of the torque. This change in diameter causes the frictional driving engagement with the annular wall to weaken until, at the predetermined limiting value of the applied torque, the frictional drive is broken and the spring slips on the wall. The torque transferred to the conductor cannot therefore exceed the predetermined limiting value.

The conductor preferably passes within the confines of the inner annular wall coaxially with the spring, while the spring is held on the outer wall, for example by a tang on the spring engaging in a recess, for example an axially-aligned slot, in the outer wall, for rotation with the handle at all levels of applied torque.

The electrical conductor preferably has its leading end in the form of an electrode which may be helical, for example a single or double helix.

Most preferably, the electrode projects from a carrier around which the spring extends in frictional contact, and an end portion of the spring engages in a recess in an inwardly-directed face of an extension to the handle, this extension being in the form of a socket which receives the carrier. Thus, the extension and carrier may be generally co-axial and radially spaced from one another with the spring between their opposing faces. In this way, the instrument can be made in sturdy and compact form, which is of considerable advantage in fetal monitoring instruments.

The torque limiting means is preferably disposed adjacent the electrode at the leading end of the instrument.

By providing the torque limiting means the electrode can be rotated to penetrate the fetal scalp as with conventional instruments, but on encountering a predetermined resistance at the desired limit of insertion the torque limiting device prevents the electrode turning further in response to increasing torque applied to the handle. The penetration of the electrode can thus be controlled.

BRIEF DESCRIPTION OF THE DRAWINGS

FIG. 2 is a section through the head portion of the instrument of FIG. 1;

FIG. 3 is a side view of the head portion shown in FIG. 2;

FIG. 4 is a front view corresponding to FIG. 3; and

FIG. 5 is a top plan view corresponding to FIG. 3.

DESCRIPTION OF THE PREFERRED EMBODIMENT

Figure 1:
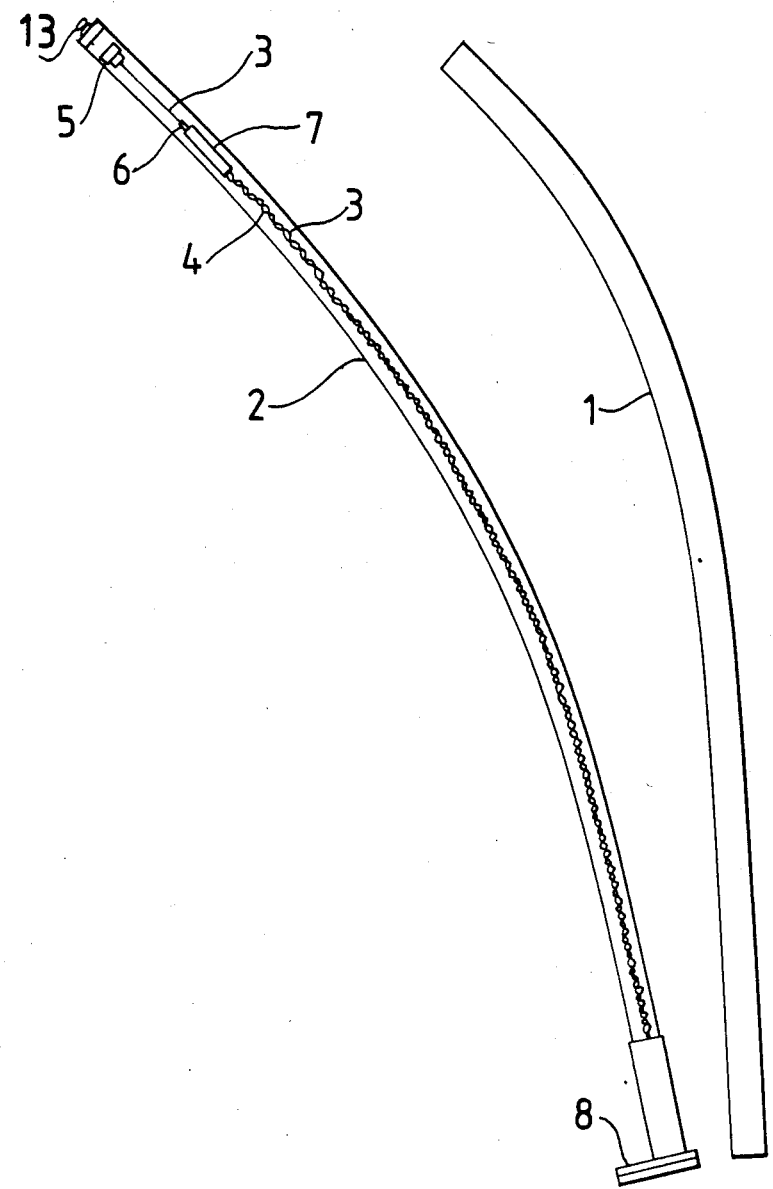
FIG. 1 is a general view of a medical instrument of this invention with the drive tube removed from the guide sheath.

Referring to FIG. 1, the instrument of this embodiment of the invention has an outer guide sheath 1 of plastics material which slidingly receives a drive tube 2 also formed of plastics material. A pair of electrical wires 3, 4 extend within the drive tube 2, one of the wires 3 being insulated and connected to an electrode head 5 and the other wire 4 being connected to an electrode sleeve 6 through which the first wire 3 passes. The electrode sleeve 6 is partly encased within a plastics collar 7.

The drive tube 2 has at its end remote from the electrode head 5 a winged drive member 8 for rotation of the drive tube 2 within the guide tube 1.

The electrode head 5 is in the form of two plastics moldings 10, 11 fitting one within the other along a portion of their length. The outer molding 11 has a pair of flats 9 which engage with corresponding internal faces in the leading end of the drive tube 2, although the drive tube 2 can be withdrawn from the head 5 and is freely slidable relative to it and the sleeve 6.

The inner molding 10 is recessed to receive a plug 12 from which extend a pair of electrodes 13 (FIG. 1) in double-helix formation. Ridges 14 serve to retain the plug in position. The wire 3 is connected to the electrodes 13 and extends through a central bore 15 in the inner molding 10 into the drive tube 2.

The inner and outer moldings 10, 11 are radially spaced from one another to form an annular gap 16 within which a helical spring 17 extends in frictional contact with the inner molding 10. The spring 17 is anchored at one end to the outer molding 11 by means of a tang 18 at the end of the spring 17 engaging in a narrow linear groove 19 in the outer molding 11.

In use, the electrode head 5 is engaged with the drive tube 2 so that the wires 3, 4 extend through the tube 2 and the electrodes 13 project from one end of the tube 2. The drive tube is then passed into the guide tube 1, and the assembled instrument is passed along the female body passage until the electrodes 13 at the leading end come against the scalp of the fetus. The drive tube 2 is then rotated to cause the electrodes to penetrate the scalp, by virtue of their helical shape. The rotational drive is transmitted from the drive tube 2 to the electrodes 13 by the engagement of the flats 9 on the molding 11 with the corresponding faces on the tubes 2, and by the frictional drive through the spring 17.

The direction of the spring's helix is such that as the electrodes 13 penetrate the scalp the spring tends to open so that its frictional contact with the inner molding 10 is lessened. At low resistance to penetration of the electrodes 13, however, this reduction in frictional contact still allows the torque from the drive tube 2 to be transmitted to the inner moulding and electrodes.

When the resistance to the electrodes' penetration increases, i.e. when the electrodes 13 are fully inserted in the foetal scalp, the torque from the drive shaft causes the spring 17 to open further to the extent that the frictional contact with the inner molding 10 is insufficient for the inner molding 10 to be rotated against the molding 10 and the spring 17 slips round the molding 10. Thus a torque limit exits, above which additional applied torque is not transmitted to the electrodes 13, and the fetal scalp is protected against excessive rotation of the drive tube 2.

When the electrodes 13 are fully inserted the guide tube 1 and drive tube 2 are removed, exposing the electrode sleeve 6 for contact with the mother. Monitoring can then be performed.

To remove the electrodes 13, the drive tube 2 is passed over the wires 3, 4 until its leading end meets the head 5 and engages against the flats 9. The drive tube 2 is then rotated in a direction which will withdraw the electrodes 13 from the scalp, and in this case the torque applied causes the spring 17 to tighten against the inner molding 10, providing positive drive for the molding 10 and electrodes 13. When the electrodes are free of the scalp the instrument is withdrawn.

Modifications and improvements may be incorporated without departing from the scope of the invention.

I claim:

1. An electrode assembly for fetal monitoring comprising:
    a rotatable elongate drive member, said drive member having a forward end and a rear end;
    a rotatable handle disposed on said rear end of said drive member for rotating said drive member;
    an electrode holder, said electrode holder being mounted on said forward end of said drive member, said electrode holder having inner and outer relatively rotatable molded members, said outer molded member being connected to and rotatable with said drive member;
    an electrically conductive electrode mounted on said inner molded member of said electrode holder, said electrode projecting from said inner molded member of said electrode holder and being rotatable with said inner molded member of said electrode holder;
    means for electrically connecting the electrically conductive electrode to a monitoring device; and
    a torque limiting means for limiting the amount of torque applied to said electrode by said drive member, said torque limiting means having a resiliently deformable member, said deformable member extending within an annular passage formed between said inner molded member and said outer molded member of said electrode holder, said deformable member being in frictional engagement with said inner molded member and held against rotation relative to said outer molded member so that relative rotation of said deformable member between said molded members causes deformation of said deformable member to limit the extent of frictional engagement and prevent over rotation of said electrode.

2. The electrode assembly of claim 1 wherein said resiliently deformable member is a helical spring.

3. The electrode assembly of claim 2 wherein said spring includes a tang means for holding said spring on said outer molded member for rotation with said drive member both above and below a predetermined limiting value.

4. The electrode assembly of claim 1 wherein said electrode is a double helix electrode.

* * * * *